United States Patent [19]

Schleicher et al.

[11] Patent Number: 5,095,205
[45] Date of Patent: Mar. 10, 1992

[54] SPECTROANALYTICAL SYSTEM

[75] Inventors: Robert G. Schleicher, Winchester; Bruce C. Fitz-Patrick, Franklin; Paul M. Moran, Framingham; David L. Pfeil, Winthrop, all of Mass.

[73] Assignee: Thermo Jarrell Ash Corporation, Waltham, Mass.

[21] Appl. No.: 662,930

[22] Filed: Mar. 1, 1991

[51] Int. Cl.$^5$ ............................................. G01J 3/50
[52] U.S. Cl. ..................................... 250/226; 356/326; 356/315
[58] Field of Search ................ 250/226; 356/306, 311, 356/312, 315, 317, 326, 328, 331-334

[56] References Cited

U.S. PATENT DOCUMENTS

| | | | |
|---|---|---|---|
| 3,532,429 | 10/1970 | Hughes | 350/162 |
| 3,586,441 | 6/1971 | Smith | 356/97 |
| 3,600,571 | 8/1971 | Chisholm | 356/96 |
| 4,214,835 | 7/1980 | Roos | 356/306 |
| 4,391,523 | 7/1983 | Hildebrand et al. | 356/306 |
| 4,469,441 | 9/1984 | Bernier | 356/334 |
| 4,867,562 | 9/1989 | Oishi | 356/319 |
| 4,930,892 | 6/1990 | Hadbawnik | 356/328 |
| 4,995,725 | 2/1991 | Riedel et al. | 356/334 |
| 5,018,856 | 5/1991 | Harnly et al. | 356/312 |
| 5,035,505 | 7/1991 | Tsukada et al. | 356/312 |

Primary Examiner—David C. Nelms
Assistant Examiner—S. Allen
Attorney, Agent, or Firm—Fish & Richardson

[57] ABSTRACT

A spectroanalytical system with a plurality of radiation sources and structure defining an analysis region that includes means for thermally energizing a sample material to be analyzed. Analysis beam path defining structure includes means for passing a radiation beam from a radiation source along the analysis beam path through the analysis region for modification by sample material in the analysis region. Analysis structure includes radiation dispersing structure arranged to disperse radiation in the analysis beam path with a spectrum and a radiation sensor. First transducer structure moves the dispersing structure relative to the beam path to apply a selected portion of the radiation dispersed by the dispersing structure to the radiation sensor. Source selector structure is disposed in the analysis beam for selecting radiation from one of the radiation sources along the analysis beam path, second transducer structure is coupled to the source selector structure for directing radiation from a particular radiation source along the analysis beam path, and control structure coordinately operates the two transducer structures to apply a particular dispersed wavelength of radiation from the selected radiation source to the radiation sensor.

19 Claims, 6 Drawing Sheets

SPECTROANALYTICAL SYSTEM

BACKGROUND AND SUMMARY OF THE INVENTION

This invention relates to spectroanalytical systems, and more particularly to spectroanalytical systems of the type that employ absorption phenomena.

It is frequently desirable to accurately determine several different elemental constituents of a sample in a single sample run of short duration.

In accordance with one aspect of the invention, there is provided a spectroanalytical system with a plurality of radiation sources and structure defining an analysis region that includes means for thermally energizing a sample material to be analyzed. Analysis beam path defining structure includes means for passing a radiation beam from a radiation source along the analysis beam path through the analysis region for modification by sample material in the analysis region. Analysis structure includes radiation dispersing structure arranged to disperse radiation in the analysis beam path with a spectrum and a radiation sensor. First transducer structure moves the dispersing structure relative to the beam path to apply a selected portion of the radiation dispersed by the dispersing structure to the radiation sensor. Source selector structure is disposed in the analysis beam path for selecting radiation from one of the radiation sources along the analysis beam path, second transducer structure is coupled to the source selector structure for directing radiation from a particular radiation source along the analysis beam path, and control structure coordinately operates the two transducer structures to apply a particular dispersed wavelength of radiation from the selected radiation source to the radiation sensor.

In a preferred embodiment, the optical system includes a bank of cassettes containing up to eight hollow cathode lamps, a galvanometer driven mirror for lamp selection, a high-resolution monochromator with a galvanometer driven grating for line selection that can traverse its entire wavelength range of greater than five hundred nanometers in less than one hundred (e.g., twenty milliseconds, a dual beam optical pathway, and a high sensitivity photomultiplier detector. Wavelength calibration is accomplished via a mercury reference lamp which is monitored via a retractable mirror.

The grating galvanometer is synchronized with the hollow cathode lamp selection mirror control galvanometer, and the accuracy of both galvanometer drives is continuously and automatically verified by the controller throughout the analytical process. Optional double beam optics utilize a second retractable mirror which is automatically moved into the analytical beam by the controller prior to the sample measurement to execute a reference beam measurement and then automatically retracted to measure the sample beam with optimal light efficiency.

The system can be configured with a single lamp mount, one four-lamp cassette or two four-lamp cassettes. Up to eight elements can be measured in an unattended run using similar single element lamps, and more than sixteen elements can be measured when multi-element (dual-element) lamps are used. The choice of elements to determine concurrently by flame atomic absorption analysis is based on the recommended flame oxidant, either air or nitrous oxide. The choice of an element pair for furnace atomic absorption is a function of the temperature necessary to volatilize the element from the graphite surface. The system can incorporate various sample input systems, including, for example the monitoring of the effluent from a chromatographic column.

Other features and advantages of the invention will be seen as the following description of a particular embodiment progresses, in conjunction with the drawings, in which.

DESCRIPTION OF PARTICULAR EMBODIMENT

Figure 1:
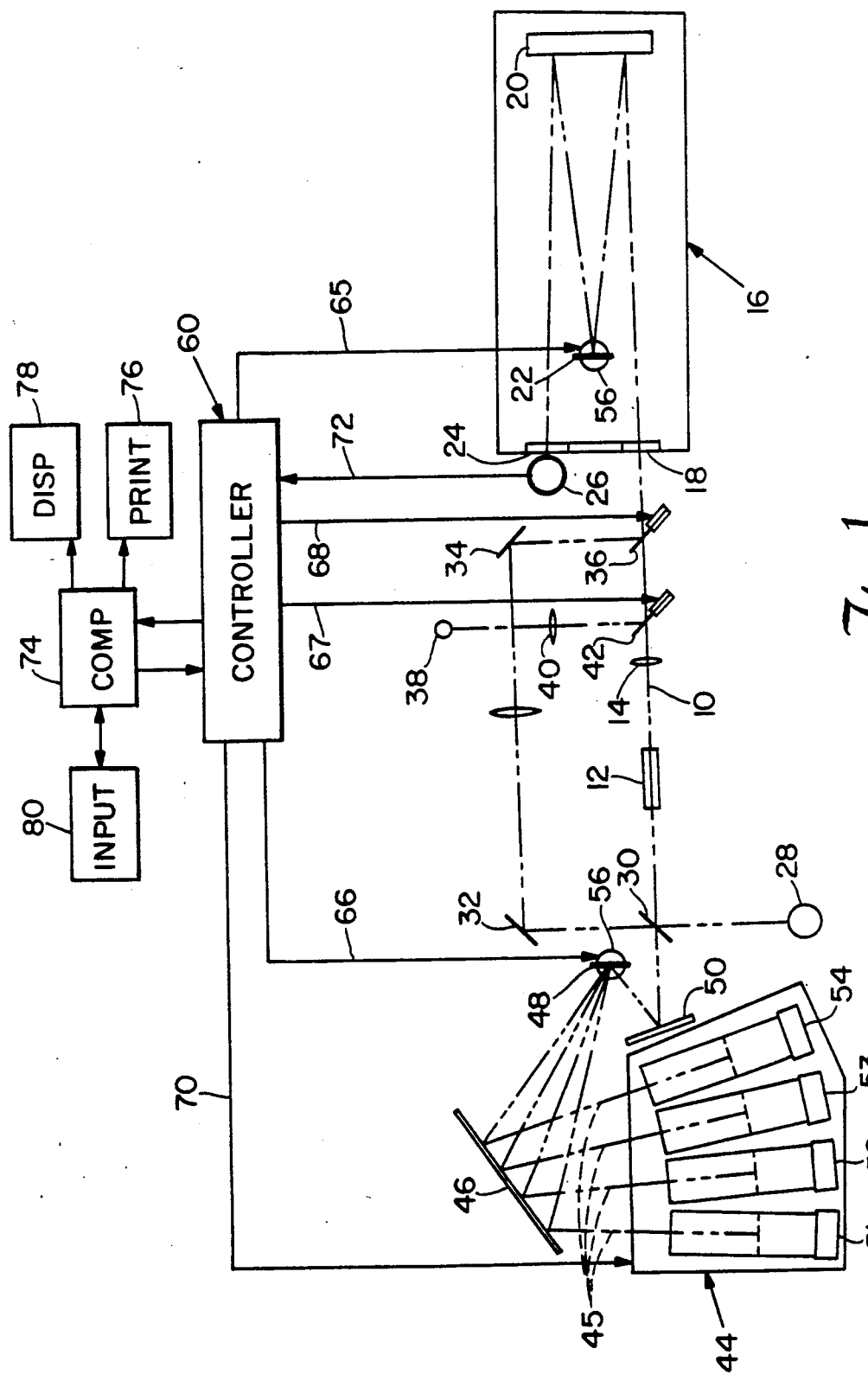
FIG. 1 is a diagram of a spectroanalytical system in accordance with the invention.

With reference to FIG. 1, the atomic absorption system there shown includes analysis beam path 10 on which is disposed an analysis region that includes thermal excitation structure 12 such as a flame atomizer or furnace, lens 14, and one third meter Ebert monochromator 16 that has entrance slit defining structure 18, mirror 20, 800 grooves per millimeter dispersion grating 22, exit aperture defining structure 24 and photomultiplier tube sensor 26. Slit structures 18 and 24 may be of the type shown in U.S. Pat. No. 3,508,813, the disclosure of which is expressly incorporated herein by reference. The system is capable of flame atomic emission spectroscopy as well as atomic absorption analysis, and is equipped for excitation of elements by either flame or furnace; the flame atomizer can be furnished with burners for both air/acetylene and nitrous oxide/acetylene flames.

Optional supplemental elements include a reference beam system that includes deuterium arc source 28, mirrors 30, 32, 34 and retractable mirror 36; and a wavelength calibration system that includes mercury source 38, lens 40 and retractable mirror 42.

Figure 4:
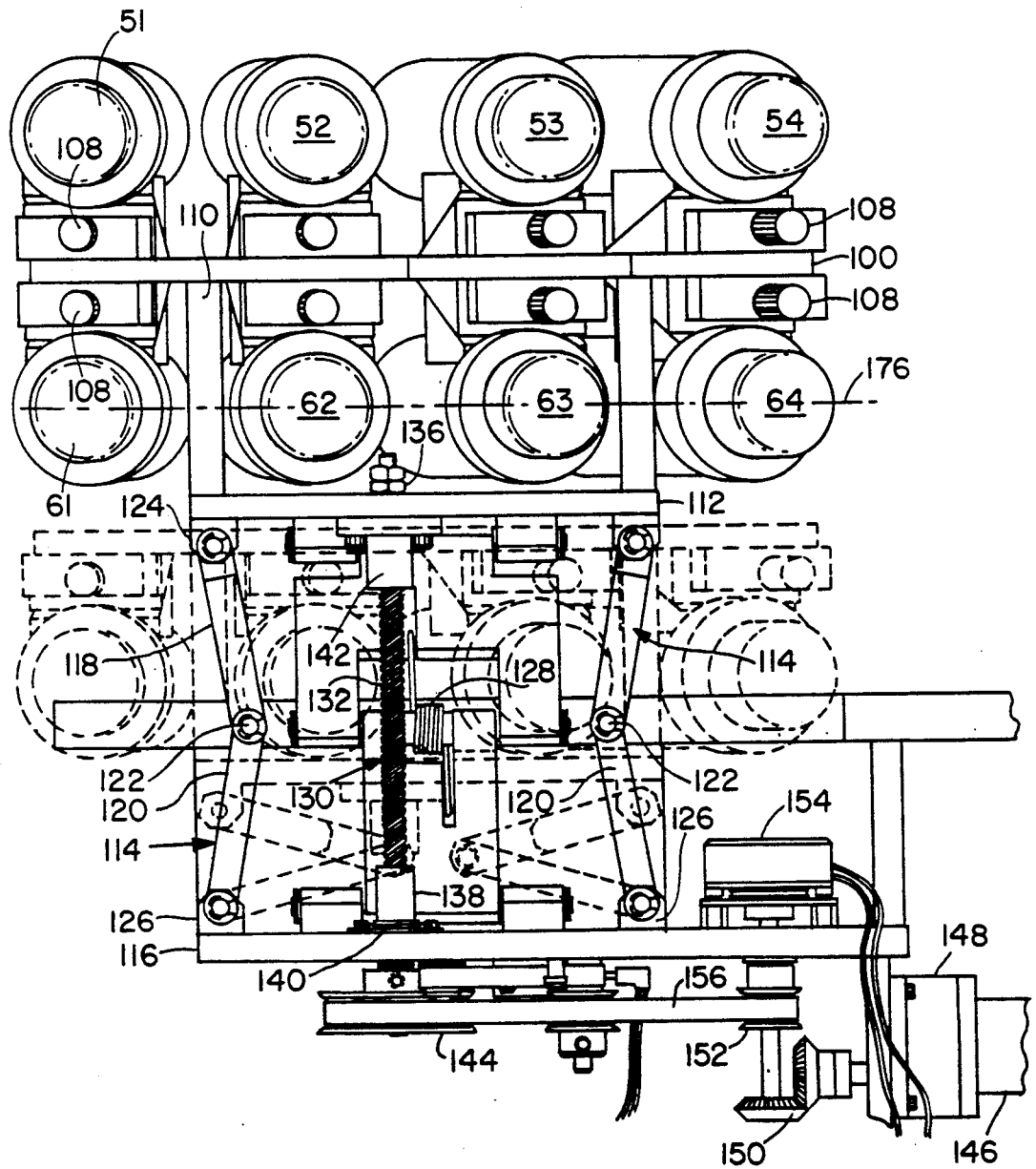
FIG. 4 is a front elevational view of the source assembly shown in FIG. 3.

Two arrays of hollow cathode lamps 51-54, 61-64 (FIG. 4) are supported on elevator assembly 44 and either array may be positioned by the elevator assembly 44 so that the beams 45 of its lamps are directed at planar reflector 46, for reflection to selector mirror 48 and toroidal mirror 50 to direct radiation along beam path 10 through the analysis region to monochromator 16. Hollow cathode lamps 51-54 may be arsenic, selenium, thallium and lead, for example; and the hollow cathode lamps 61-64 may be of other types, some or all of which may be multiple-element lamps. Grating 22 and selector mirror 48 are individually mounted on support and drive assemblies 56 that respond to signals, preferably digital signals of at least sixteen binary digits, from controller 60 over lines 65, 66, respectively. Controller 60 also generates signals over lines 67, 68 to control retractable mirrors 36, 42; over lines 70 to control source positioning elevator assembly 44; and receives signals over line 72 from sensor 26 for application to computer 74 for data processing and application of outputs to printer 76 and display 78, and control signals from input keyboard 80. Thus, the entire optical system—including the elevator assembly 44 that positions the lamps 51-54 and 61-64, the galvanometer drives 56, the retractable mirrors 36, 42, and the parameter settings on the photomultiplier 26—is under microprocessor control. The analyzer can run unattended, and in such operation, standards and samples can be rerun, different groups of elements can be analyzed, and the sample volume can be varied.

Figure 2:
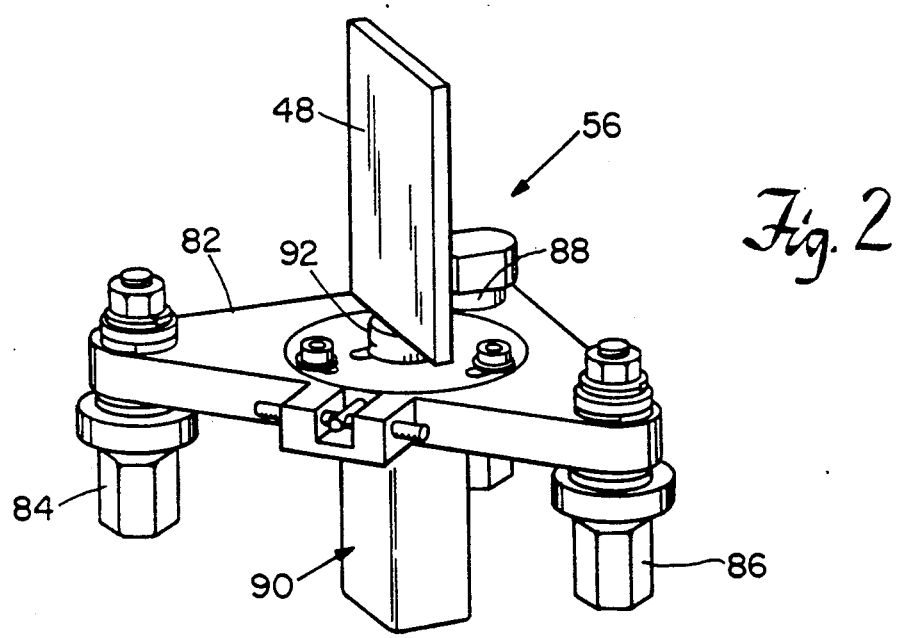
FIG. 2 is a perspective view of a source selector mirror assembly employed in the system shown in FIG. 1.
Figure 3:
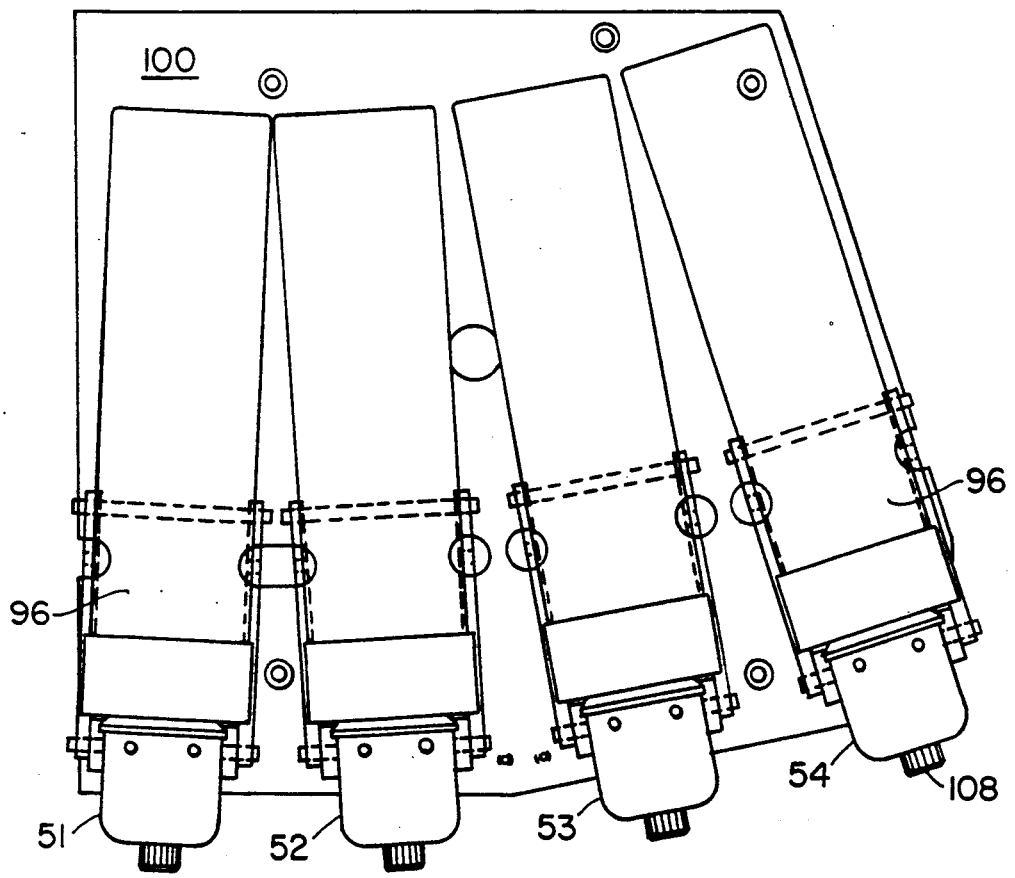
FIG. 3 is a top view of a source assembly employed in the system of FIG. 1.
Figure 5:
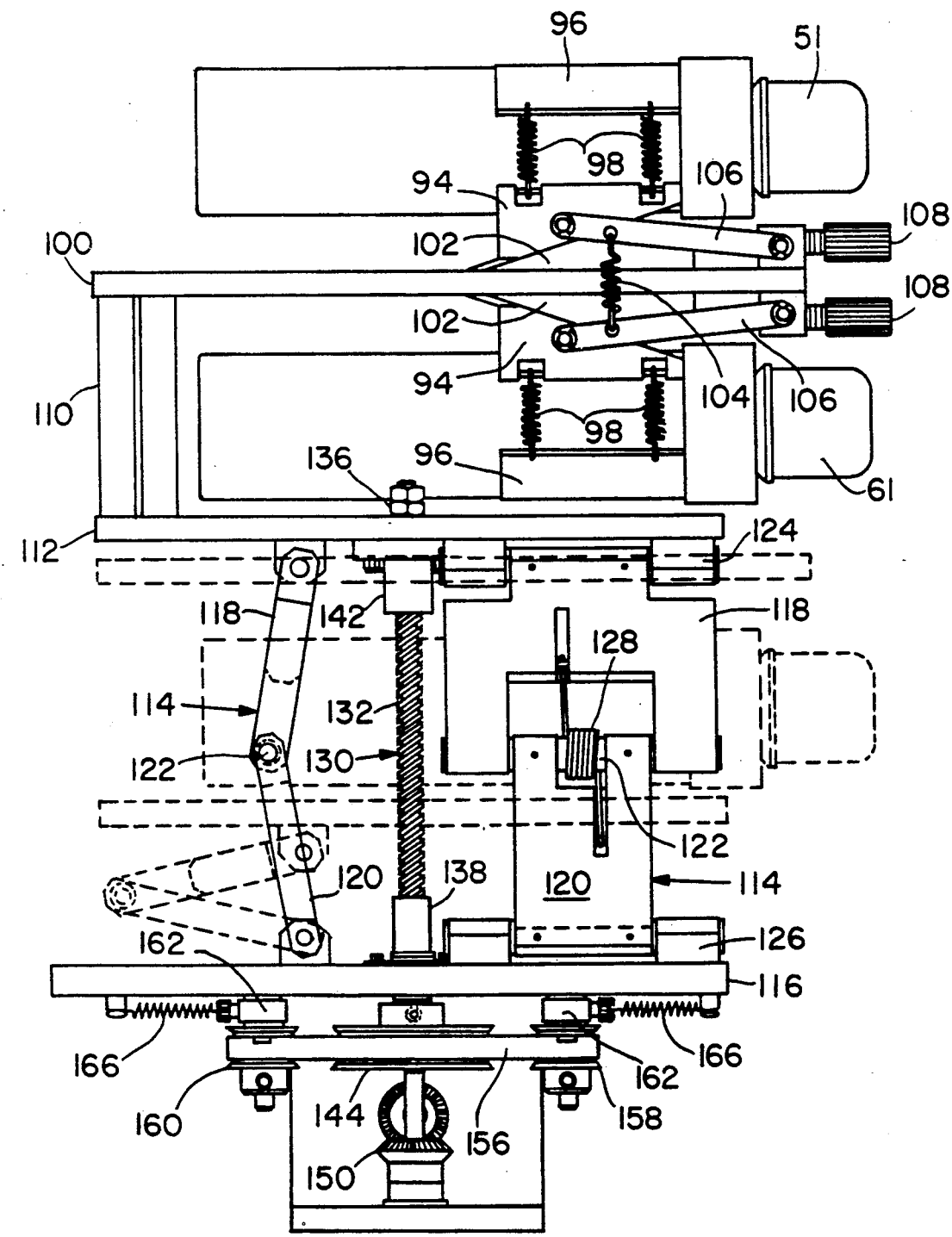
FIG. 5 is a side elevational view of the source assembly shown in FIG. 3.
Figure 6:
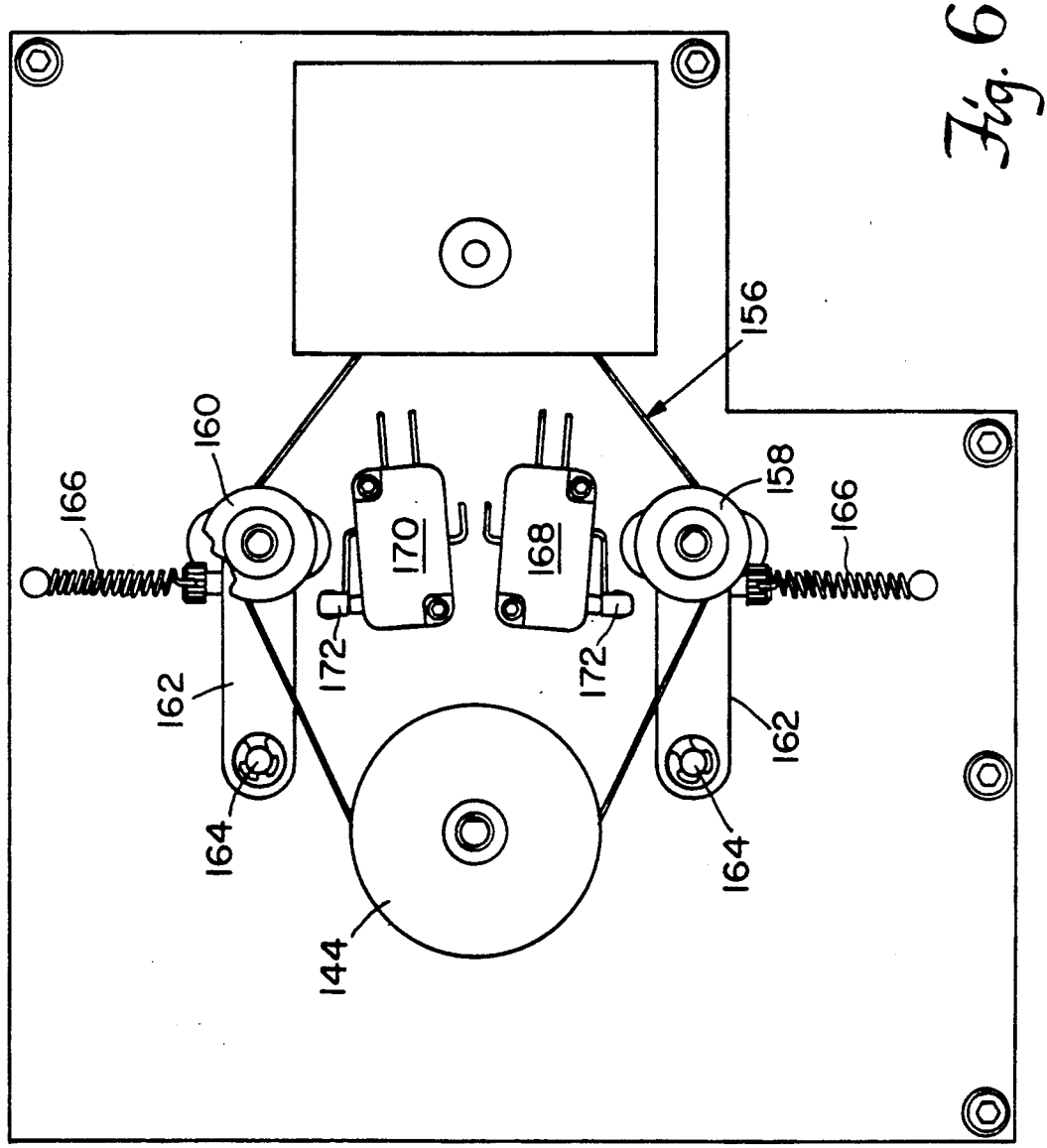
FIG. 6 is a bottom plan view of the source assembly shown in FIGS. 3-5 showing aspects of the drive system.

Each drive assembly 56 is of the type shown in FIG. 2, and includes support plate 82 of triangular configuration that is mounted on upstanding posts 84, 86, 88 that provide two mutually independent tilt adjustments. Carried on plate 82 is limited rotation motor 90 which includes upwardly projecting shaft 92 to which the grating 22 or the mirror 48, respectively, is clamped. Each transducer 90 rotates its optical component over an angle of plus or minus 8½ degrees in response to digital input signals. Further details of drive assembly 56 may be had with reference to Bernier U.S Pat. No. 4,469,441, the disclosure of which is expressly incorporated herein by reference. During initial installation, monochromator 16 may be calibrated from the mercury source 38, the hollow cathode lamps 51-54 and 61-64 aligned vertically, and a peak reading for each source identified and stored in the memory of computer 74. Further aspects of elevator assembly 44 and the arrays of the hollow cathode tubes 51-54 and 61-64 may be seen with reference to FIGS. 3-5. As is shown in FIG. 5, each hollow cathode tube is secured on seat 94 by clamp plate 96 and biasing springs 98. Mounted on aluminum plate 100 are ramp members 102, and seats 94 are biased against their respective ramp members by springs 104 that are connected to arms 106 which are connected to seats 94 and are also connected to adjustment mechanisms 108 for varying the relative vertical positionings of the several hollow cathode lamps 51-54 and 61-64.

Platform 100 of the elevator assembly 44 is supported by posts 110 on plate 112 that in turn is supported by scissor arm assemblies 114 from fixed base 116. Each scissor arm assembly 114 includes arm members 118, 120 that are pivoted together at 122 and secured by brackets 124 to platform 112 and brackets 126 to base 116. Coil spring 128 of each assembly 114 provides a biasing force that acts between arms 118 and 120 to oppose the force of gravity.

Also coupled between platform 112 and base 116 is drive screw assembly 130 that includes 0.6 centimeter diameter Teflon impregnated hard anodized aluminum drive shaft 132 that has thread 134 with a lead of about 1.2 centimeters and about six threads per centimeter. The upper end of shaft 132 is of reduced diameter and carries upper stop 136. Brass lower stop sleeve 138 is at the base of shaft 132 just above self-aligning bearing 140. Threadedly carried on shaft 132 is acetal (Delrin) nut 142. Shaft 132 extends through self-aligning bearing 140 in base 116 and is coupled to drive pulley 144.

Figure 7:
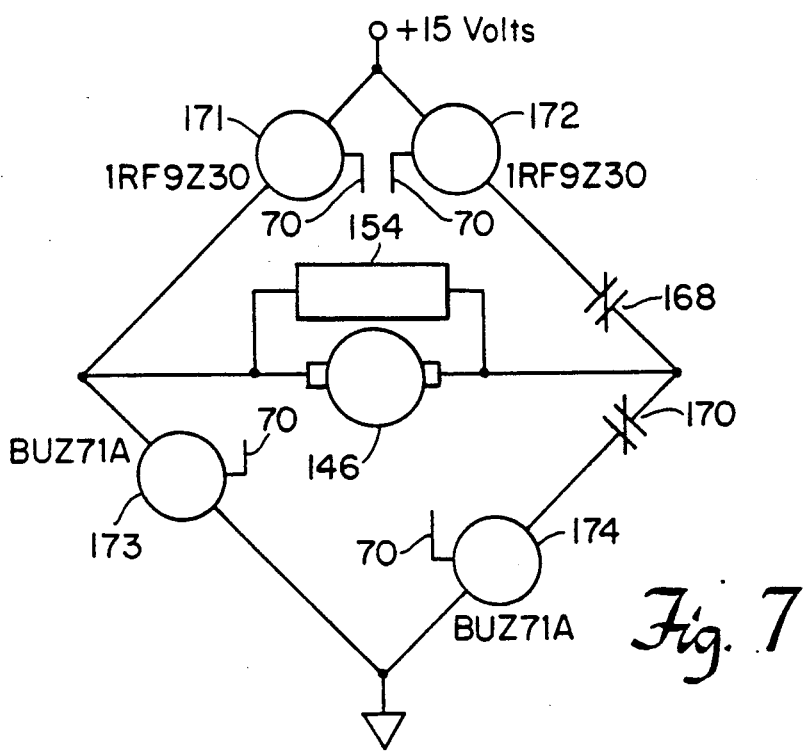
FIG. 7 is a diagram of circuitry employed in the drive system shown in FIGS. 6.

Further details of the elevator drive system may be seen with reference to FIGS. 4-7. That drive system includes 12 volt DC motor 146 with a 60:1 gear reducer 148 that is connected through gears 150 to drive pulley 152. Coupled to drive pulley 152 is brake 154. 0.6 centimeter wide timing belt 156 is trained over idler pulleys 158, 160, each of which is carried on actuator link 162 which in turn is mounted for rotation about pivot 164 and biased outwardly by spring 166. Lever type switches 168, 170 each includes an actuator 172 that is aligned with the adjacent actuator link 162. Switches 168, 170 are interconnected in motor and brake bridge circuit as shown in FIG. 7. That circuit includes controllers 171-174 that receive control signals from controller 60 over lines 70. Motor 146 is energized in the clock-wise direction by closing controllers 171 and 174; and in the reverse direction by closing controllers 172 and 173; and brake 154 is concurrently energized and held in its open (released) state. If the load on drive screw 132 increases, due to nut 142 reaching either the upper stop 136 or the lower stop 138 (or if the movement of plate 112 encounters modest resistance (of about three pounds) due, for example, to an obstruction), tension on the drive belt 156 increases in the drive direction, and the corresponding idler pulley 160 is pivoted against biasing force of its spring 166 to actuate the corresponding interlock switch 168 or 170 and de-energize motor 146 and release brake 154 to hold shaft 132 in position.

The overall travel of the hollow cathode tube elevator plate 100 (from stop 136 to stop 138) is about six centimeters and requires about six seconds. In the upper position (with nut 142 abutting upper stop 136), the lower bank of hollow cathode tubes 61-64 is disposed in the optical plane 176 of beam path 10. In the lower position (with nut 142 abutting lower stop 138), the upper bank of hollow cathode tubes 51-54 are disposed in the optical plane 176.

In this travel, motor 146 is energized in the clockwise direction to move nut 142 downwardly by closing of controllers 171 and 174 in response to a signal on line 70. When nut 142 contacts stop 138, the tension in that portion of drive belt 156 trained over idler pulley 160 increases and pivots link 162 against the force of spring 166 against actuator 172 of switch 170 to open that switch and de-energize motor 146 and apply brake 154 to hold plate 100 in the lower (dotted) position with the upper bank of hollow cathode tubes 51-54 disposed in optical plane 176.

In that position, a spectrochemical analysis is initiated by aspirating the sample to be analyzed into the flame of the flame atomizer 12. Mirror 48 is positioned by its drive 56 to pass radiation from a selected one of the bank of hollow cathode tubes 51-54 through the analysis region 12 and entrance slit 18 of monochromator 16. Concurrently, grating 22 is positioned by signals from controller 60 over line 65 to select the corresponding wavelength at the exit slit 24 for sensing by photomultiplier tube 26. The drive voltage range is plus or minus 5 volts and the digital input signal excursion is plus or minus 131,072 steps. The desired grating position determines the binary member input and that value is used by controller 60 in the grating equation to determine the correct binary input required to produce the grating angle for the desired wavelength. The drive transducers 56 for mirror 48 and grating 56 are repeatedly adjusted during an analysis of the sample. The grating 22 is positioned within one millidegree by its drive transducer and the mirror 98 is positioned within ten millidegrees by its drive transducer. Due to the speed of the galvanometer driven movement of the mirror 48 and gating 22, a sequence of beams from the four hollow cathode tubes is passed through the aspirated sample in the flame of the atomizer 12 many times during the course of one flame aspiration cycle.

The galvanometer drives for wavelength and lamp selection are fast (from 185 nanometers wavelength to 900 nanometers wavelength in twenty milliseconds) and wavelength selection has high resolution (in the range of 0.08 to two nanometers). The analysis system is like an inexpensive plasma spectrometer with extraordinary sensitivity and can be configured to determine a large number of elements is a single unattended run with each element being determined at PPB levels. Each sample is presented in succession with beams from four hollow cathode lamps. Because of the speed of the galvanometer-driven mirror and grating drives, the sample is presented with each beam many times during the course of one flame aspiration or single atomization cycle.

Figure 8:
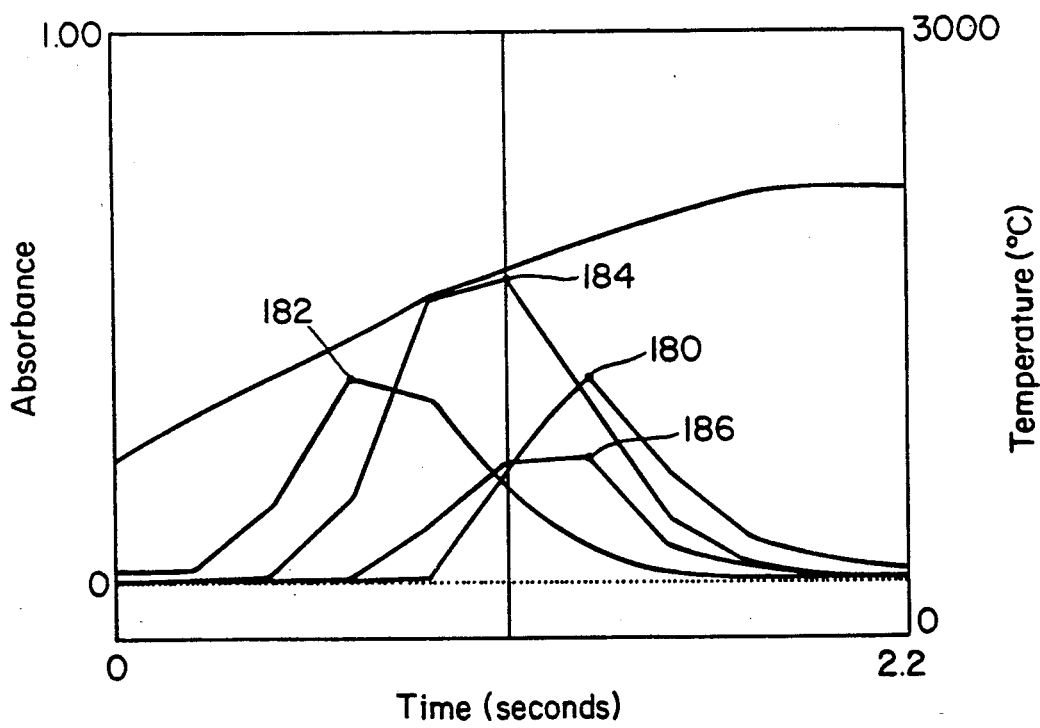
FIG. 8 is a graph of a multi-element measurement made with the system shown in FIG. 1.

A graph of a typical sample analysis (analysis of water with a furnace atomizer for arsenic, selenium, lead and thallium) obtained with the analyzer system of the invention, utilizing one of two four-lamp arrays, is shown in FIG. 8. That graph shows an arsenic peak 180 of 0.200 absorbance units, a selenium peak 182 of 0.221 absorbance units; a lead peak 184 of 0.557 absorbance units; and a thallium peak 186 of 0.169 absorbance units. The analysis duration was about 2.2 seconds, and the lead peak 184 occurred at about 1.1 seconds into the analysis cycle and at a temperature of 1829° C.

While a particular embodiment of the invention has been shown and described, various modifications will be apparent to those skilled in the art, and therefore, it is not intended that the invention be limited to the disclosed embodiment, or to details thereof, and departures may be made therefrom within the spirit and scope of the invention.

What is claimed is:

1. A spectroanalytical system comprising
   a plurality of radiation sources,
   structure defining an analysis region that includes means for thermally energizing a sample material to be analyzed,
   analysis beam path defining structure includes means for passing a radiation beam from a radiation source along said analysis beam path through said analysis region for modification by sample material in said analysis region,
   analysis structure including a radiation sensor, radiation dispersing structure arranged to disperse radiation in said analysis beam path in a spectrum,
   first transducer structure for moving said dispersing structure to apply a selected portion of the radiation dispersed by said dispersing structure to said radiation sensor,
   source selector structure disposed in said analysis beam path for selectively directing radiation from one of said radiation sources along said analysis beam path,
   second transducer structure coupled to said source selection structure for selecting a particular radiation source, and
   control structure for coordinately operating said first and second transducer structures to apply a particular dispersed wavelength of radiation from the selected radiation source to said radiation sensor for analysis of thermally energized sample material in said analysis region.

2. The system of claim 1 wherein said analysis structure includes monochromator structure that includes structure defining an entrance aperture, and structure defining an exit aperture, and said dispersing structure is arranged to disperse radiation passing through said entrance aperture structure in a spectrum for application of a selected wavelength of said spectrum to said exit aperture structure for sensing by said radiation sensor.

3. The system of claim 1 wherein each said transducer structure includes a limited rotation motor.

4. The system of claim 1 wherein said first transducer structure is operable to move said dispersing structure over a wavelength range of greater than five hundred nanometers in less than one hundred milliseconds.

5. The system of claim 1 wherein said dispersing structure is a diffraction grating that has at least one hundred grooves per millimeter.

6. The system of claim 1 wherein said control structure includes a controller for generating a digital input signal of at least sixteen binary digits that specifies a desired angular position of said dispersing structure.

7. The system of claim 1 wherein each said radiation source is of the hollow cathode tube type, and said analysis region includes means for generating a flame and means for aspirating the sample material to be analyzed into said flame.

8. The system of claim 1 wherein said plurality of radiation sources are disposed in planar array, said source selector structure includes a mirror, and said second transducer structure is a limited rotation motor adapted to rotate said mirror about a fixed axis perpendicular to the plane of said planar array.

9. The system of claim 1 and further including first retractable mirror structure in said analysis beam path, and wavelength calibration means including a mercury reference lamp monitorable by said analysis structure via said first retractable mirror structure.

10. The system of claim 9 and further including second retractable mirror structure in said analysis beam path, and double beam optics, and wherein said control structure is adapted to move said second retractable mirror into the analytical beam prior to the sample measurement to execute a reference beam measurement and then to retract said second mirror from said analysis beam path to measure the sample beam with optimal light efficiency.

11. The system of claim 10 wherein said analysis structure includes monochromator structure that includes structure defining an entrance aperture, and structure defining an exit aperture, and said dispersing structure is arranged to disperse radiation passing through said entrance aperture structure in a spectrum for application of a selected wavelength of said spectrum to said exit aperture structure for sensing by said radiation sensor.

12. The system of claim 11 wherein each said transducer structure includes a limited rotation motor.

13. The system of claim 12 wherein said first transducer structure is operable to move said dispersing structure over a wavelength range of greater than five hundred nanometers in less than one hundred milliseconds.

14. The system of claim 13 wherein said dispersing structure is a diffraction grating that has at least one hundred grooves per millimeter.

15. The system of claim 14 wherein said source selector structure includes a mirror, and said second transducer structure is a limited rotation motor adapted to rotate said mirror about a fixed axis.

16. The system of claim 15 wherein said control structure includes a controller for generating a first digital input signal of at least sixteen binary digits that specifies a desired angular position of said diffraction grating, and a second digital input signal that specifies a desired angular position of said mirror.

17. The system of claim 16 wherein each said radiation source is of the hollow cathode tube type, and said analysis region includes means for generating a flame and means for aspirating the sample material to be analyzed into said flame.

18. The system of claim 17 wherein said plurality of radiation sources are disposed in planar array, and said second transducer structure is adapted to rotate said mirror about a fixed axis perpendicular to the plane of said planar array.

19. A spectroanalytical system comprising
an array of radiation sources,
structure defining an analysis region that includes means for thermally energizing a sample material to be analyzed,
analysis beam path defining structure includes means for passing a radiation beam from a radiation source along said analysis beam path through said analysis region for modification by sample material in said analysis region,
monochromator structure includes structure defining an entrance aperture, structure defining an exit aperture, radiation dispersing structure arranged to disperse radiation passing through the entrance aperture structure in a spectrum for transmission to the exit aperture structure,
first transducer structure for moving said dispersing structure relative to the optical axis of said monochromator system to apply a selected portion of the radiation dispersed by said dispersing structure to said exit aperture structure,
optical selector structure disposed in said analysis beam path for selectively directing radiation from one of said radiation sources along said analysis beam path,
second transducer structure coupled to said optical selection structure for moving that structure to select a particular radiation source, and
control structure for coordinately operating said two transducer structures to apply a particular dispersed wavelength of radiation from the selected radiation source at said exit aperture structure.

* * * * *